US008380545B2

(12) United States Patent
Chen et al.

(10) Patent No.: US 8,380,545 B2
(45) Date of Patent: *Feb. 19, 2013

(54) SYSTEMS AND METHODS FOR DETERMINING CONCENTRATIONS OF EXPOSURE

(75) Inventors: Han Chen, San Jose, CA (US); Weimin Dong, Palo Alto, CA (US); Andrew Coburn, Oakland, CA (US)

(73) Assignee: Risk Management Solutions, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/764,045

(22) Filed: Apr. 20, 2010

(65) Prior Publication Data

US 2010/0205016 A1    Aug. 12, 2010

Related U.S. Application Data

(63) Continuation of application No. 10/797,143, filed on Mar. 11, 2004, now Pat. No. 7,707,050.

(51) Int. Cl.
*G06Q 40/00* (2012.01)
(52) U.S. Cl. ............ 705/4; 705/39; 707/102; 707/104.1
(58) Field of Classification Search .................. 705/2–4, 705/39; 707/102, 104
See application file for complete search history.

(56) References Cited

U.S. PATENT DOCUMENTS

| 5,553,214 | A | * | 9/1996 | Marks et al. .................. 345/441 |
| 5,839,113 | A | | 11/1998 | Federau et al. |
| 5,855,005 | A | | 12/1998 | Schuler et al. |
| 6,077,869 | A | | 6/2000 | Sui et al. |
| 6,223,122 | B1 | | 4/2001 | Hancock et al. |
| 6,405,134 | B1 | | 6/2002 | Smith et al. |
| 6,513,019 | B2 | | 1/2003 | Lewis |
| 6,556,991 | B1 | | 4/2003 | Borkovsky |
| 6,678,615 | B2 | | 1/2004 | Howard et al. |
| 6,686,917 | B2 | | 2/2004 | Tarr |
| 6,741,993 | B1 | | 5/2004 | Zitaner et al. |
| 7,009,619 | B2 | | 3/2006 | Akitsune et al. |
| 7,107,285 | B2 | * | 9/2006 | von Kaenel et al. ................... 1/1 |
| 7,949,548 | B2 | | 5/2011 | Mathai et al. |
| 2001/0027437 | A1 | | 10/2001 | Turbeville et al. |

(Continued)

FOREIGN PATENT DOCUMENTS

| AU | 2005/220387 | 9/2005 |
| AU | 2010/257377 | 1/2011 |

(Continued)

OTHER PUBLICATIONS

U.S. Appl. No. 10/797,143, Office Action mailed Jul. 27, 2009.

(Continued)

*Primary Examiner* — Michelle Le
(74) *Attorney, Agent, or Firm* — Jackson & Co., LLP

(57) ABSTRACT

A system and method are provided for identifying exposure concentrations. The process of determining exposure concentrations may include organizing exposure data, defining parameters, determining elevated exposure concentrations, and providing output results. The exposure data may relate to at least geographical locations, policies, accounts, portfolios, treaties, and other exposure data. The parameters may be defined to include at least an area of analysis, a region of interest, a threshold amount, results parameters, and other parameters. The exposure concentration may include at least defining and locating exposure locations using various techniques. The results may be presented using textual, graphical, or other display schemes. The output may be configured to convey information such as positional accuracy of an identified area, exposure accumulation in a defined area, and other information.

25 Claims, 10 Drawing Sheets

U.S. PATENT DOCUMENTS

| | | | |
|---|---|---|---|
| 2002/0042770 A1 | 4/2002 | Slyke et al. | |
| 2002/0080138 A1 | 6/2002 | Tarr | |
| 2002/0173980 A1 | 11/2002 | Daggett et al. | |
| 2002/0188556 A1* | 12/2002 | Colica et al. | 705/38 |
| 2003/0009287 A1 | 1/2003 | Howard et al. | |
| 2003/0120568 A1 | 6/2003 | Chacko et al. | |
| 2003/0167125 A1 | 9/2003 | Seeman et al. | |
| 2003/0195776 A1 | 10/2003 | Moore et al. | |
| 2004/0064346 A1 | 4/2004 | Schneider et al. | |
| 2004/0117358 A1 | 6/2004 | Von Kaenel et al. | |
| 2004/0193494 A1 | 9/2004 | Zitaner et al. | |
| 2004/0210594 A1 | 10/2004 | Gosselin | |
| 2005/0007450 A1 | 1/2005 | Hill et al. | |
| 2005/0131828 A1 | 6/2005 | Gearhart | |
| 2005/0144114 A1 | 6/2005 | Ruggieri et al. | |
| 2005/0159882 A1 | 7/2005 | Howard et al. | |
| 2005/0187881 A1 | 8/2005 | McGiffin et al. | |
| 2005/0192963 A1 | 9/2005 | Tschiegg et al. | |
| 2005/0203825 A1 | 9/2005 | Angle et al. | |
| 2005/0246222 A1* | 11/2005 | Bailey | 705/10 |
| 2007/0203759 A1 | 8/2007 | Mathai et al. | |
| 2007/0214023 A1 | 9/2007 | Mathai et al. | |

FOREIGN PATENT DOCUMENTS

| | | |
|---|---|---|
| JP | 06-043804 | 2/1994 |
| JP | 09-305108 | 11/1997 |
| JP | 11-211839 | 8/1999 |
| JP | 11-314865 | 11/1999 |
| JP | 2001/005834 | 1/2001 |
| JP | 2003/204568 | 7/2003 |
| JP | 2003/271052 | 9/2003 |
| JP | 2004/020219 | 1/2004 |
| JP | 2004/062248 | 2/2004 |
| WO | WO-02/19091 | 3/2002 |
| WO | WO-2005/088496 | 9/2005 |
| WO | WO-2007/098268 | 8/2007 |
| WO | WO-2007/103402 | 9/2007 |

OTHER PUBLICATIONS

U.S. Appl. No. 10/797,143, Office Action mailed Nov. 28, 2008.
U.S. Appl. No. 10/797,143, Office Action mailed Apr. 16, 2008.
U.S. Appl. No. 10/797,143, Office Action mailed Oct. 9, 2007.
U.S. Appl. No. 10/797,143, Notice of Allowance mailed Jan. 22, 2010.
Ha, "CAT Modeling, Forecasting Tools More Sophisticated", *National Underwriter Property & Casuality-Risk & Benefit Management*, Feb. 23, 2004, pp. 17-19.
Japanese Patent Application No. 2007-502405, English Translation of Office Action mailed Mar. 1, 2011.
Japanese Patent Application No. 2007-502405, Original Language and English Translation of Office Action mailed Aug. 3, 2010.
New Zealand Patent Application No. 550420, Examination Report mailed Sep. 14, 2007.
New Zealand Patent Application No. 574815, Examination Report mailed Feb. 17, 2009.
PCT Application No. PCT/GB2005/000947, International Preliminary Report on Patentability and Written Opinion of the International Searching Authority mailed Sep. 13, 2006.
PCT Application No. PCT/GB2005/000957, International Search Report mailed Jan. 5, 2006.

* cited by examiner

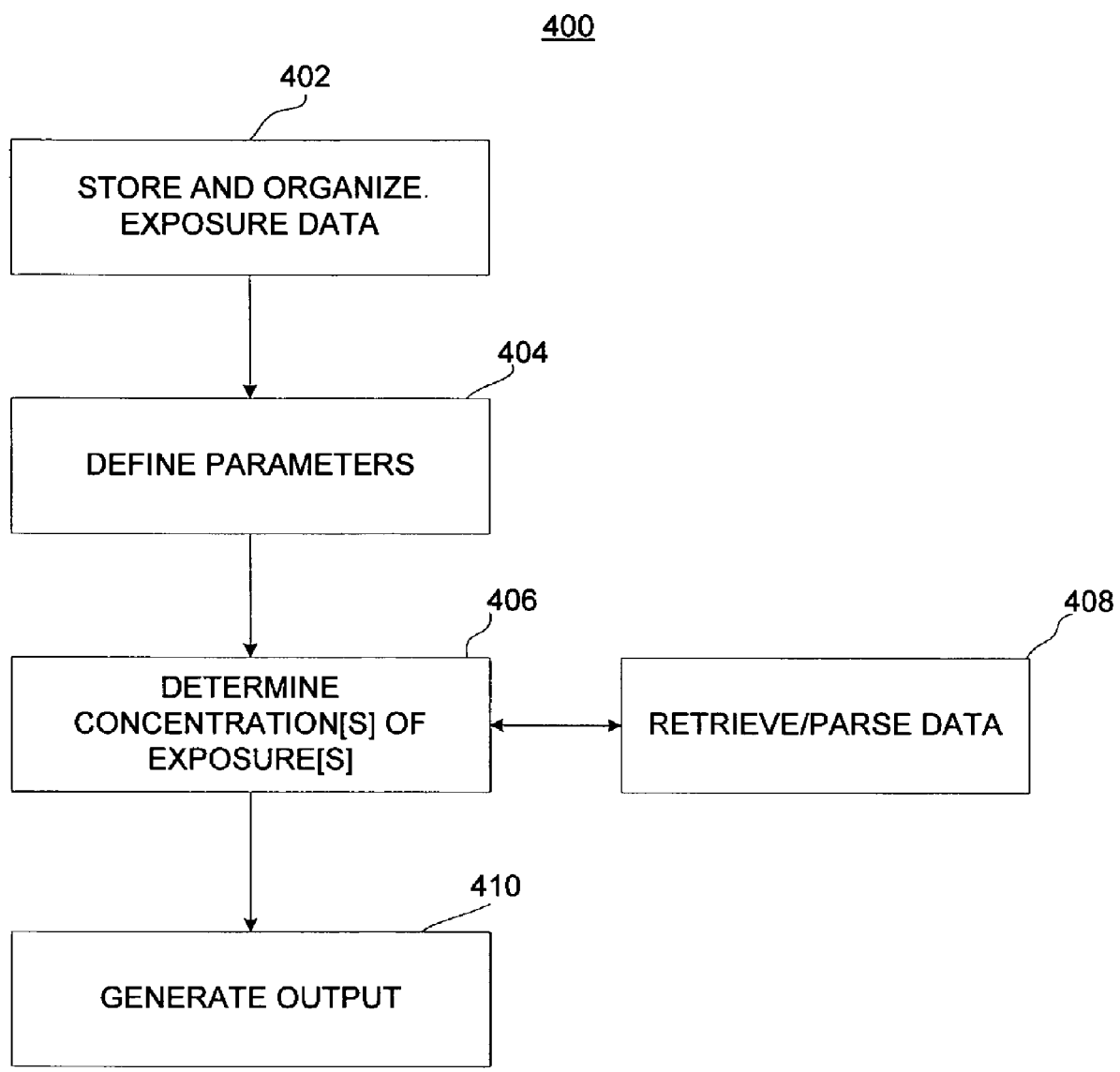

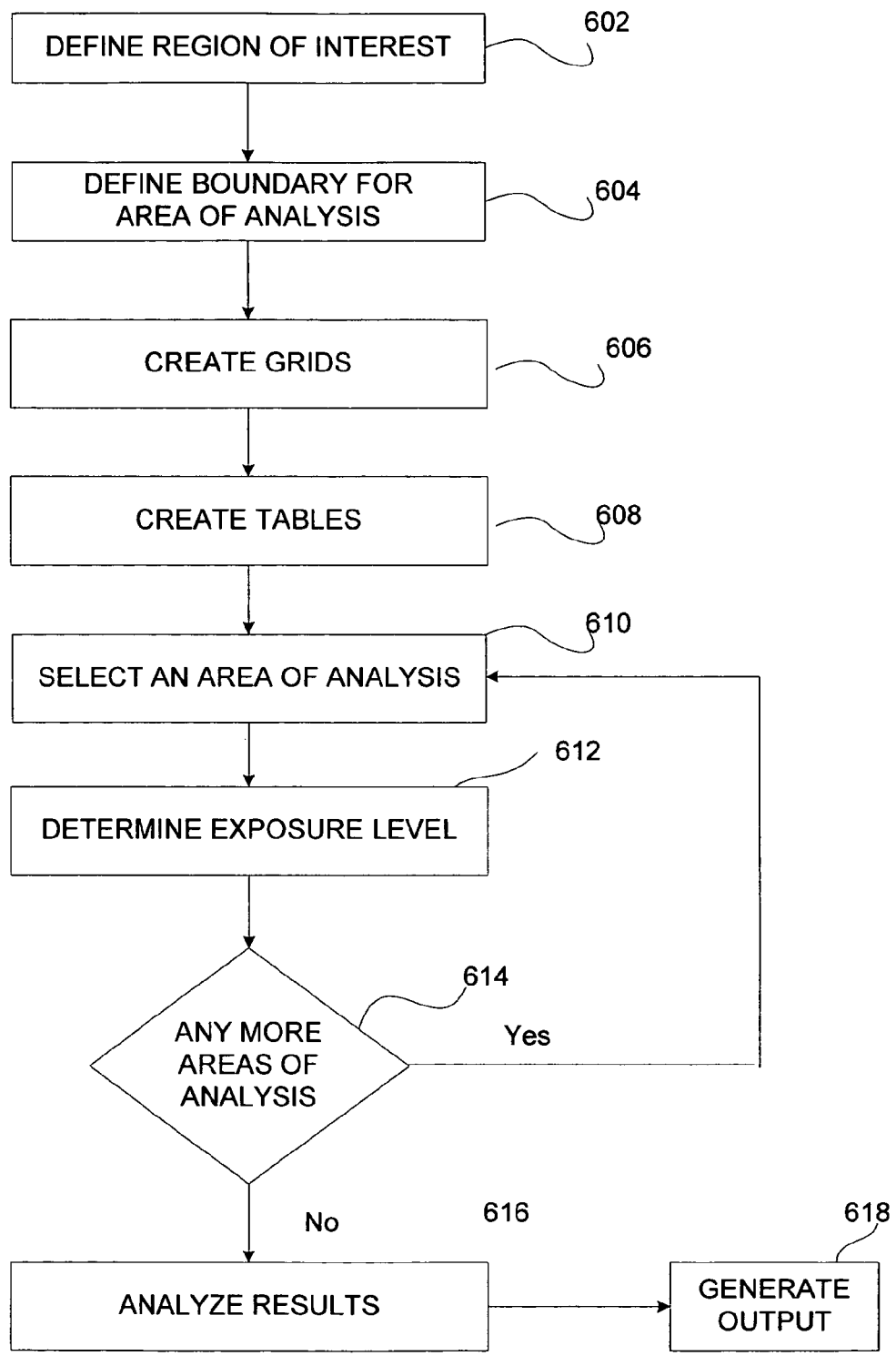

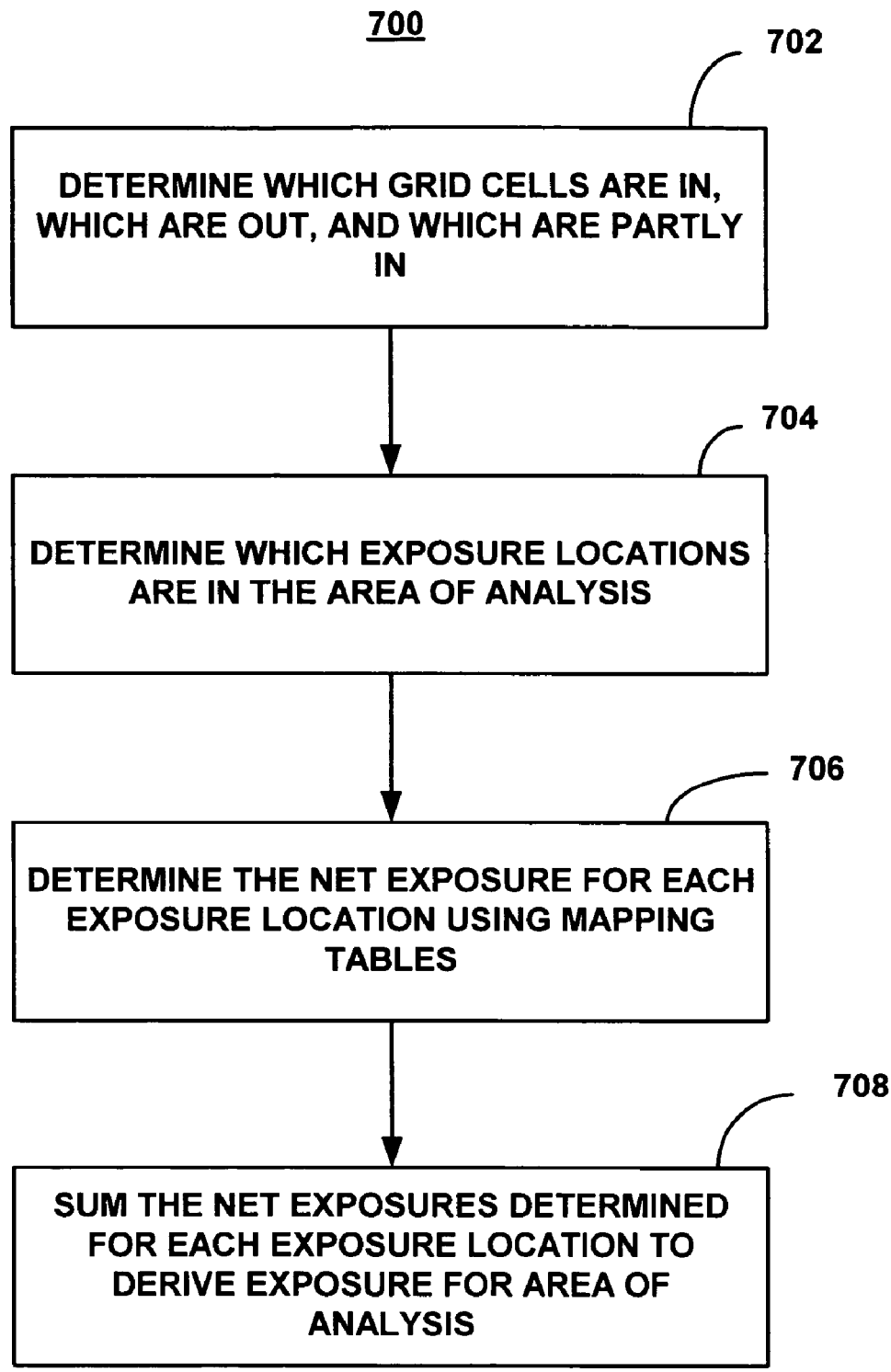

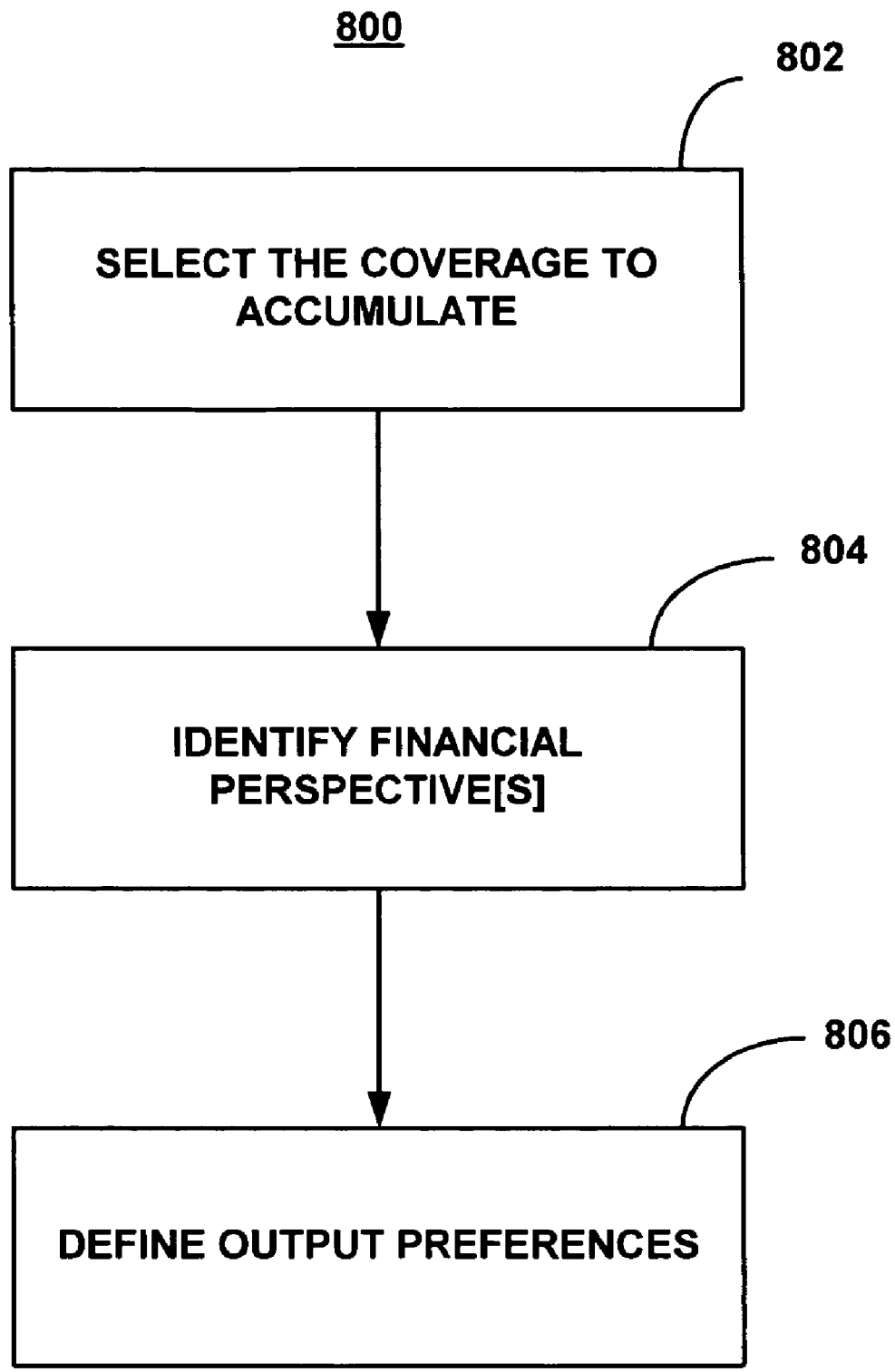

SYSTEMS AND METHODS FOR DETERMINING CONCENTRATIONS OF EXPOSURE

RELATED APPLICATIONS

The present application is a continuation of pending U.S. patent application Ser. No. 10/797,143 filed Mar. 11, 2004 entitled "Systems And Methods For Determining Concentrations Of Exposure," the disclosure of which is herein incorporated by reference for all purposes.

FIELD OF THE INVENTION

This invention relates generally to systems and methods for identifying concentrations of high liability exposures.

BACKGROUND OF THE INVENTION

It is known that models may be used in order to assess the potential liabilities of catastrophic events. These events may be either man-made or natural occurring disasters such as earthquakes, tornados, hurricanes, terrorist attacks and other disasters.

Certain industries, such as insurance companies, may find information provided by these models useful. These models may generate large amounts of data that may facilitate the determination of potential liabilities (i.e., exposure) when catastrophic events occur. In order to fully appreciate the information provided by these models, the data may be further processed and analyzed.

SUMMARY OF THE INVENTION

The present invention relates to systems and methods for identifying concentrations of exposure. Exposure may be defined as the potential financial liability that may be incurred by a party or parties.

According to one aspect of the invention, systems for determining concentrations of exposure is provided. These systems, sometimes referred to as "exposure concentration analyzer systems," may include a database, an input/output device, and various modules. These modules may include, for example, a database manager module, an accumulation analysis module, a parameter builder module or other modules.

According to another aspect of the invention, the database may be used to store exposure data. The stored exposure data may include, for example, exposure data relating to geographical locations, policies, accounts, portfolios, treaties, and other information that may be used in analyzing and/or processing exposure data.

According to another aspect of the invention, the database may include exposure data relating to property loss, workmen's compensation and/or both. The property loss data may be related to specific perils such as earthquakes, windstorms, tornado/hail, fire, terrorism, and other natural or manmade perils.

According to another aspect of the invention, mapping tables may be stored in the database. The mapping tables may be an account mapping table, a location mapping table, a policy mapping table, and/or other tables that may be used for analyzing and/or processing exposure data.

According to another aspect of the invention, the database may store one or more financial perspectives. Financial perspectives may define the structure of financial liabilities. That is, may define, for example, which parties are financially responsible for what portion of a loss or for what type of loss.

According to another aspect of the invention, exposure data stored in the database may be linked to data for one or more portfolios, one or more accounts, one or more policies, and/or one or more locations.

According to another aspect of the invention, the database manager module is used to retrieve, organize and/or store exposure data in the database. The exposure data may include, for example, exposure data relating to geographic locations, mapping tables, financial perspectives, accounts, locational data, policies, and other data.

According to another aspect of the invention, the parameter builder module may be used to define a region of interest. The region of interest is a geographical area that may be analyzed in order to determine a concentration of exposure location or area.

According to another aspect of the invention, the parameter builder module may be used to define whether the exposure concentrations are related to property loss, workmen's compensation loss or both.

According to another aspect of the invention, the parameter builder module may be used to define areas of analysis and grid width. The areas of analysis are the geographical areas or locations within the region of interest that are individually analyzed to determine whether one or more of the areas have high (or the highest) exposure concentrations. A mapping grid may be used in order to facilitate determination of concentrations of exposure.

According to another aspect of the invention, the accumulation analysis module may use an exhaustive search approach in determining concentrations of exposure. The exhaustive search approach is a reiterative process that determines the exposure amounts for each area of analysis in the region of interest and compares the exposure amounts to determine the area of analysis having high (or the highest) exposure amounts.

According to another aspect of the invention, the exhaustive search approach may use grids in order to determine exposure of an area of analysis. The grids may be useful in determining which exposure locations belong to an area of analysis. The exposure locations may be geographical locations with some level of exposure.

According to another aspect of the invention, the accumulation analysis module may use an analytical approach in determining concentrations of exposure. The analytical approach may be a mathematical approach using density functions in order to determine peaks and valleys in the concentrations of exposure.

According to another aspect of the invention, the input/output device may generate results in a text format, in a graphical format and/or in a mapping format.

According to another aspect of the invention, the exposure concentration analyzer system may be located locally at the system user's computer device or on the user's network. Alternatively, the exposure concentration analyzer system may be remotely located from a system user. The user may communicate with the system via a client application and via a communication link comprising of networks such as the Internet, an intranet, a LAN, a WAN, a PSTN, or other networks used for communication.

According to another aspect of the invention, the exposure concentration analyzer system may further include a module for specific area analysis, damaged footprint analysis and/or building level analysis. In specific area analysis, a location may be selected and accumulation for a specified area around the location may be determined. In damaged footprint analysis, a system user may select a location, define an area around the location and determine the levels of damage for different sections of the area surrounding the location. An accumulation may then be determined for the entire area based on different damage levels.

According to another aspect of the invention, the exposure concentration analyzer system may be a standalone system.

According to another aspect of the invention, methods for determining concentrations of exposure may be provided. The methods may include an operation for storing and organizing exposure data, an operation for defining parameters, an operation for determining high (or the highest) exposure concentrations, and an operation for generating an output.

According to another aspect of the invention, the operation for storing and organizing exposure data may include linking the exposure data being stored to one or more portfolios, one or more accounts, one or more policies, and/or one or more locations.

According to another aspect of the invention, the exposure data stored may be linked to one or more financial perspectives.

According to another aspect of the invention, the operation for storing and organizing data may further include an operation for storing portfolio, account, policy, location, treaty, and/or financial perspective data.

According to another aspect of the invention, the operation for determining concentrations of exposure may further include an operation for retrieving and parsing exposure data. The exposure data may be associated with a location, an account, a policy, and/or a portfolio. The exposure data may be linked to one or more types of perils such as earthquake, windstorm, tornado/hail, fire, tidal wave, terrorism, and other natural or manmade perils. The exposure data may further include exposure data relating to property loss, workmen's compensation and/or both.

According to another aspect of the invention, the operation for defining parameters may include an operation for defining areas of analysis. This may be accomplished, for example, by defining boundaries for areas of analysis, which may be circles, rectangles, squares or other geometric shapes. If circles or other curved shapes are used, then one or more radii may be provided.

According to another aspect of the invention, the operation for defining parameters may further include an operation for defining a region of interest. The region of interest may be a geographical area that the methods for determining concentrations of exposure analyzes in determining areas of high exposure concentration.

According to another aspect of the invention, the operation for determining parameters may further include an operation for determining results parameters. The results parameters may define the types of results to be displayed. For example, the results of the analysis may only show the geographical area having the highest exposure concentration or may show the top ten areas.

According to another aspect of the invention, the operation for defining parameters may include an operation for defining a threshold amount. The threshold amount may be defined so that only those areas having accumulation amounts over the threshold level will be identified. The threshold amount may be the accumulation amount that determines whether an area of analysis is considered to be an area having a high concentration of accumulation. Only those areas of analysis determined as having a high concentration of accumulation may then be displayed or highlighted when the results of the analysis are generated.

According to another aspect of the invention, the operation for defining parameters may include the operation for defining a parameter which results in only the areas of analysis having the highest accumulation amounts be identified. For example, a user and/or an administrator may designate that only the top ten areas of analysis having the highest accumulation amounts will be identified.

According to another aspect of the invention, the exposure concentration that is determined may be for property loss, workmen's compensation or both. The property loss exposure may be due to various perils such as earthquakes, tornados, terrorist attacks, windstorms, or other manmade or natural perils. Alternatively, the property loss exposure may also be the result of two or more of the perils or from all perils.

According to another aspect of the invention, the operation for determining concentration of exposure may include an operation for determining a financial perspective. The exposure of each exposure location may be linked to one or more policies, one or more accounts and/or one or more portfolios. These items, in turn, may determine a financial perspective which may define the specific liabilities (or portions thereof) of various parties for an insured property and/or workmen's compensation. Thus, a financial perspective may be used to determine the financial exposure of a party, such as an insurance company, as it relates to property loss and/or workmen's compensation loss for a particular location.

According to another aspect of the invention, the operation for storing and organizing exposure data may further include an operation for creating mapping tables. The mapping tables may be account mapping tables, policy mapping tables, location mapping table, and/or other mapping tables used in analyzing and processing exposure data.

According to another aspect of the invention, the methods for determining concentrations of exposure may further include the operation of defining and locating exposure locations. An exposure location may be any location that may be a potential financial liability. The exposure locations may identify the precise locations of exposure locations via, for example, longitude/latitude coordinates, street address, building name, zip code, and other techniques for identifying locations. The exposure locations may also be assigned to location identifications.

According to another aspect of the invention, the operation for determining concentration of exposure may further include an operation for determining a financial perspective.

According to another aspect of the invention, the operation for determining a financial perspective may use mapping tables.

According to another aspect of the invention, the operation for determining concentration of exposure may further include an operation for determining exposure amounts for one or more exposure locations. The exposure amounts may then be used to determine total exposures for one or more areas of analysis and to determine which areas of analysis have high (or the highest) exposure concentrations.

According to another aspect of the invention, the operation for determining concentration of exposure may include an exhaustive search approach. The exhaustive search approach may include an approach where the region of interest is divided into grid cells. Each grid cell may include zero, one or more exposure locations.

According to another aspect of the invention, a region of interest may be analyzed for concentrations of accumulation by arbitrarily or systematically moving a boundary for areas of analysis to different locations within the region of interest until the entire region of interest has been analyzed.

According to another aspect of the invention, the boundary area of analysis may be moved by moving the centroid of the boundary from the center of a grid cell to another grid cell center.

According to another aspect of the invention, the boundary of area of analysis may be moved by moving the boundary arbitrarily until the entire region of analysis is analyzed.

According to another aspect of the invention, the area of analysis may be a specific area or damage footprint. Within a specific area, all of the locations located within the area of analysis are assumed to receive a complete level (i.e., 100 percent) of loss. Within a damage footprint, different sections of the area of analysis may be assumed to have different levels of loss.

According to another aspect of the invention, each exposure location may be associated with a net exposure. The net exposure for an exposure location may be the actual exposure incurred by a particular party after all of the deductibles, co-insurer's share and other deductions have been subtracted from the total insured property value. The net exposure for an exposure location may be determined using a ground up approach. In a ground up approach, the exposure location first identified and based on the location, policies, accounts and portfolios associated with the location may be determined. The policies, accounts, and portfolios that are associated with the location are then reviewed to determine the net exposure (i.e., potential liability) associated with the location.

According to another aspect of the invention, the operation for determining concentration of exposure may include defining a grid width ratio. If the area of analysis is a circle, then the grid width ratio may be selected, for example, to optimize accuracy and/or speed. The grid width ratio may be preselected in that a user may not be able to determine the grid width ratio. Alternatively, a user may be allowed to change the grid width ratio.

According to another aspect of the invention, the operation for determining the concentration of exposure may utilize an analytical approach. The analytical approach may integrate a density function for areas of analysis to determine the level of exposure accumulation for each area being analyzed.

According to another aspect of the invention, the operation for generating output may include an operation for generating results in different formats. The results may be in text form listing the areas of analysis having the highest concentration of exposures for a region of interest. Alternatively, or in combination therewith, the results may show or highlight the area with the highest concentration of exposure. The results may also be shown graphically such as in a chart. The results may further be displayed on a map. For instance, the areas with the highest concentration of exposures may be highlighted on a map.

According to another aspect of the invention, the methods for determining concentrations of exposure may further comprise an operation for performing a specific area analysis, a damaged footprint analysis and/or a building level analysis. The specific area analysis may determine the total exposure of an area assuming 100 percent loss for the entire area. The damage footprint analysis determines total loss of an area with different levels of loss for different sections of the analyzed area. The building level analysis determines exposure for one or more buildings. In order to perform these analyses, profiles for each of these analyses may be created. An analysis profile may include information, such as parameters, used in performing the analysis.

Additional features and advantages of the invention are set forth in the description that follows, and in part are apparent from the description, or may be learned by practice of the invention. The objectives and other advantages of the invention are realized and gained by the structure particularly pointed out in the written description and claims thereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate embodiments of the invention and, together with the description, serve to explain the principles of the invention. In the drawings:

FIG. 4 is a process for determining concentrations of exposure according to one embodiment of the invention.

FIG. 6 illustrates operations for determining concentrations of exposure using the exhaustive search approach according to an embodiment of the invention.

FIG. 7 illustrates operations for determining the net exposure amount of an area of analysis according to an embodiment of the invention.

FIG. 8 illustrates operations that may be performed in order to create an analysis profile according to an embodiment of the invention.

DETAILED DESCRIPTION

The invention relates to systems and methods for identifying concentrations of exposure. Exposure may refer to the potential liability that may be incurred by one or more parties. The systems and methods may take exposure data as they relate to, for example, a geographic region and process the data to determine specific areas or locations within the region having high (or the highest) concentrations of exposure.

Figure 1A:
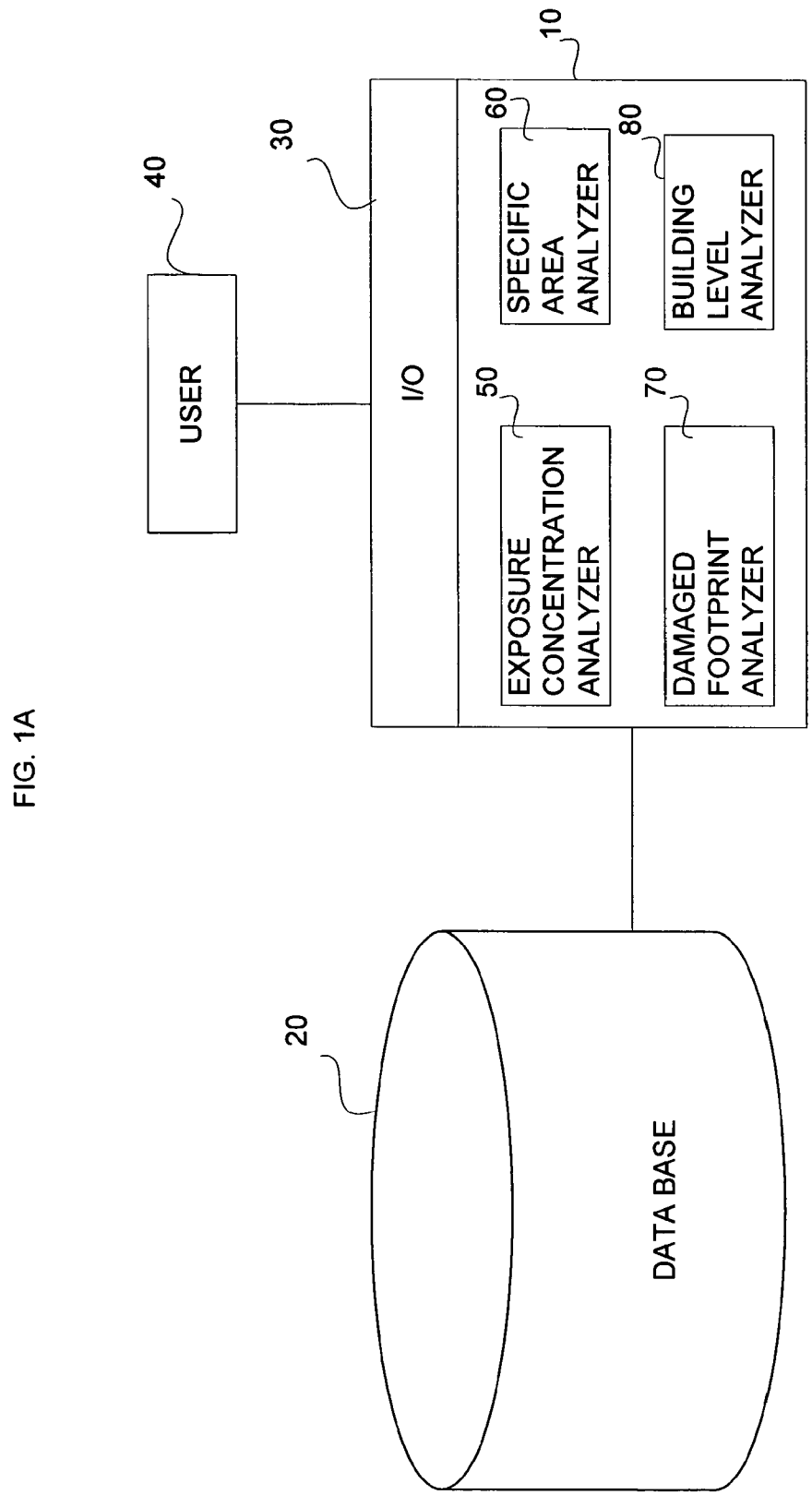
FIG. 1A is a block diagram of a financial exposure analyzing system according to one embodiment of the invention.

FIG. 1A is a block diagram that illustrates a financial exposure analyzing system 10 according to one embodiment of the invention. The exposure analyzing system 10 may include a database 20, an input/output device 30 for communicating with a user 40, and a plurality of modules (or subsystems) including an exposure concentration analyzer 50, a specific area analyzer 60, a damaged footprint analyzer 70, a building level analyzer 80, or other modules. The database 20 may store various data including exposure data, policy data, account data, portfolio data, mapping tables, financial perspectives, locational data, and other data that may be used in analyzing exposure data. The database may also store various types of mapping tables such as a policy mapping table, an account mapping table, a location mapping table, and other types of mapping tables. These tables may be useful in linking various types of data to specific geographical location. The input/output device 30 may be used to generate results of analyses in different formats. The results may be displayed as text, as graphical displays and/or as maps, or some combination thereof.

Each of the analyzer modules 50, 60, 70, and 80, may be used to provide different analyzing functions. The exposure concentration analyzer 50 may be used to identify geographical areas or locations having high (or the highest) concentrations of exposure. The specific area analyzer 60 may determine the total financial exposure for a specified geographical area. This analysis may assume complete (i.e., 100 percent) ground up property loss for the area being analyzed.

The damaged footprint analyzer 70 is similar to the specific area analyzer 60 in that both may also determine the total financial exposure for a specified area. However, the damaged footprint analyzer 70 assumes different levels of loss for different portions of the area being analyzed. For example, if the area being analyzed is a circle, the levels of loss may be structured as concentric circles (such as a bull's-eye), with each concentric circle reflecting a different level of property and casualty loss.

The building level analyzer 80 may determine exposure accumulation by building, either for all buildings within a portfolio or for a building selected by a user. In some embodiments of the invention, a user or system administrator may provide certain parameters. For instance, for the exposure concentration analyzer 50, specific area analyzer 60, and the damaged footprint analyzer 70, the areas to be analyzed must be identified. For the building level analyzer, the buildings to be analyzed must be identified. In some embodiments of the invention, each of the modules 50, 60, 70, and 80 may operate as a standalone system (independent of the other modules).

Figure 1B:
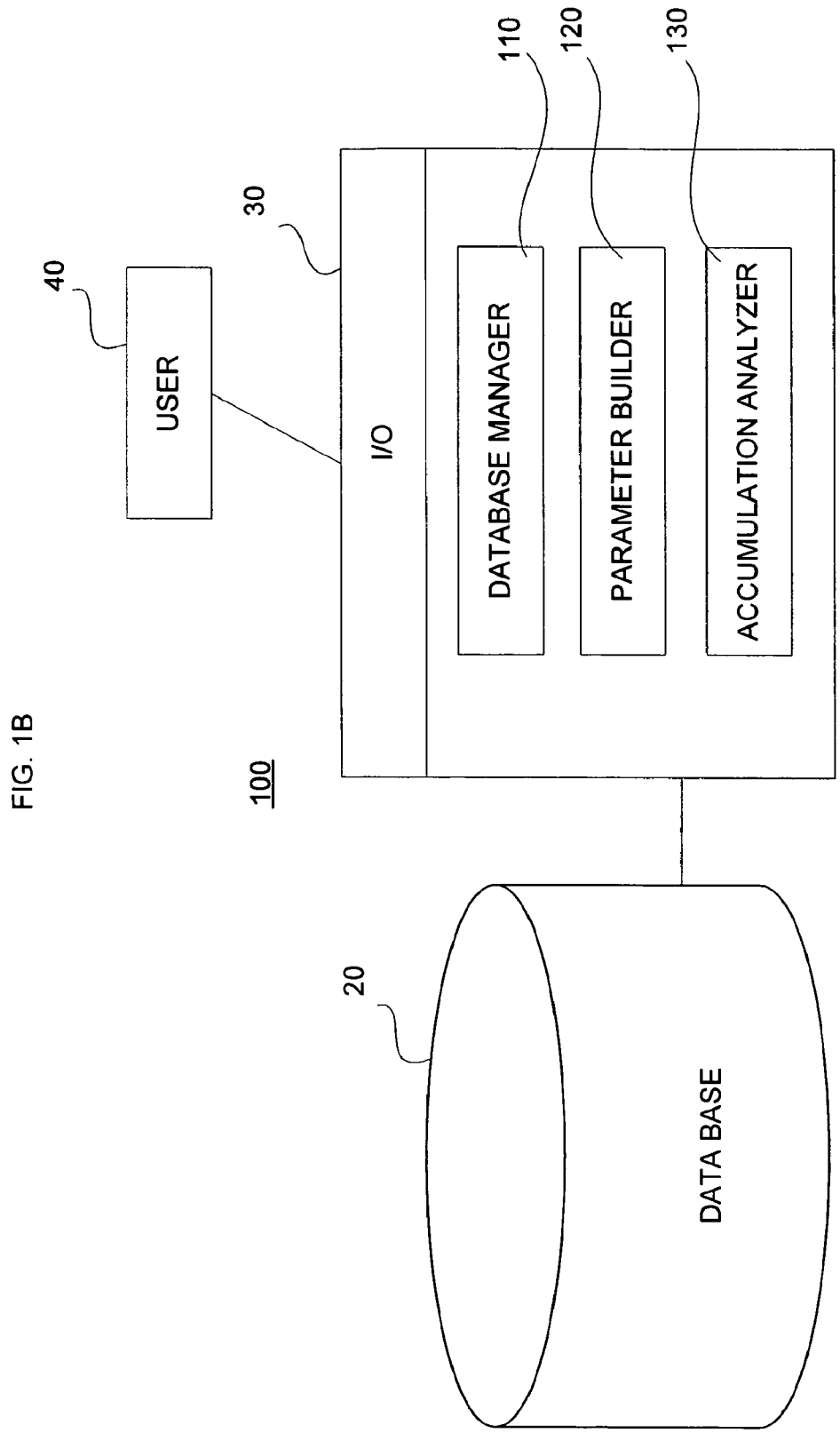
FIG. 1B is a block diagram of an exposure concentration analyzer system according to another embodiment of the invention.

FIG. 1B is a block diagram that illustrates an exposure concentration analyzer system 100, according to an embodiment of the invention. As illustrated, system 100 generally represents exposure concentration analyzer module 50 as a standalone system. The system 100 may include a database 20, an input/output device 30 for communicating with a user 40, various modules, a database manager module 110, a parameter builder module 120, and an accumulation analyzer module 130. The database manager module 110 may facilitate the retrieval, storing and parsing of data stored in the database 20. Such data may include, for example, exposure data, policy data, treaties, locational information, mapping data, financial perspectives data and other data that may be used in order to analyze and process exposure data.

The parameter builder 120 may facilitate the creation of parameters used in implementing the accumulation analyzer module 130. The accumulation analyzer 130 determines exposure amounts for one or more geographical areas or locations and determines the areas having high (or the highest) exposure concentrations. The exposure concentration analyzer system 100 may be located locally in a client system or on the user's local network. Alternatively, the exposure concentration analyzer system 100 may be remotely located from the system user 40. The user may communicate with the system 100 using a client application and via a communication link comprising of networks such as the Internet, the intranet, LAN, WAN, PSTN, or other networks used for communication.

According to one embodiment of the invention, the database 20 may be a relational database. The database may store various types of data such as data relating to exposure locations, policies, portfolios, accounts, exposures, treaties, financial perspectives, and other types of data. An exposure location may be a specific geographical location that may be associated with an exposure. In other words, exposure locations are locations whereby potential liabilities may exist. Exposure location data may include precise locational information for an exposure location. This locational information may include, for example, latitude/longitude coordinates, street address, zip code, and/or other techniques for identifying locations. The exposure location may also be assigned attributes. For example, an exposure location may be assigned attributes such as property loss exposure, workmen's compensation exposure, accounts, policies, portfolios, financial perspectives, treaties, and/or other attributes.

The data stored in the relational structure may facilitate a ground up approach in determining the net exposure of a specific location. That is, so long as the location is known, the amount of exposure for that location may be determined because the location may be linked to specific policies, portfolios, treaties, financial perspectives, and other items that may be used in determining exposure.

Actual exposure data for specific exposure locations may be stored in the database 20 or may be determined by other data stored in the database 20. For example, a policy may typically define a maximum loss amount for an insured property. However, the policy may typically also define deductibles, which will reduce the amount of liability for the insurer. The actual liability or net exposure of the insurer may be further reduced by reinsurers or other insurers who may have purchased a portion of the policy. The exposure data for a location may be related to various types of exposure including property loss and/or to workmen's compensation. The exposure relating to property loss may further include exposure relating to specific perils. Perils may be, for example, earthquakes, windstorms, tornado/hail, fire, terrorism, and other natural or manmade perils. A policy may cover only damages as a result of a particular peril but not for another. The database 20 may also store exposure data that is the sum of exposures from one or more perils or for all perils or some portion thereof.

Figure 2:
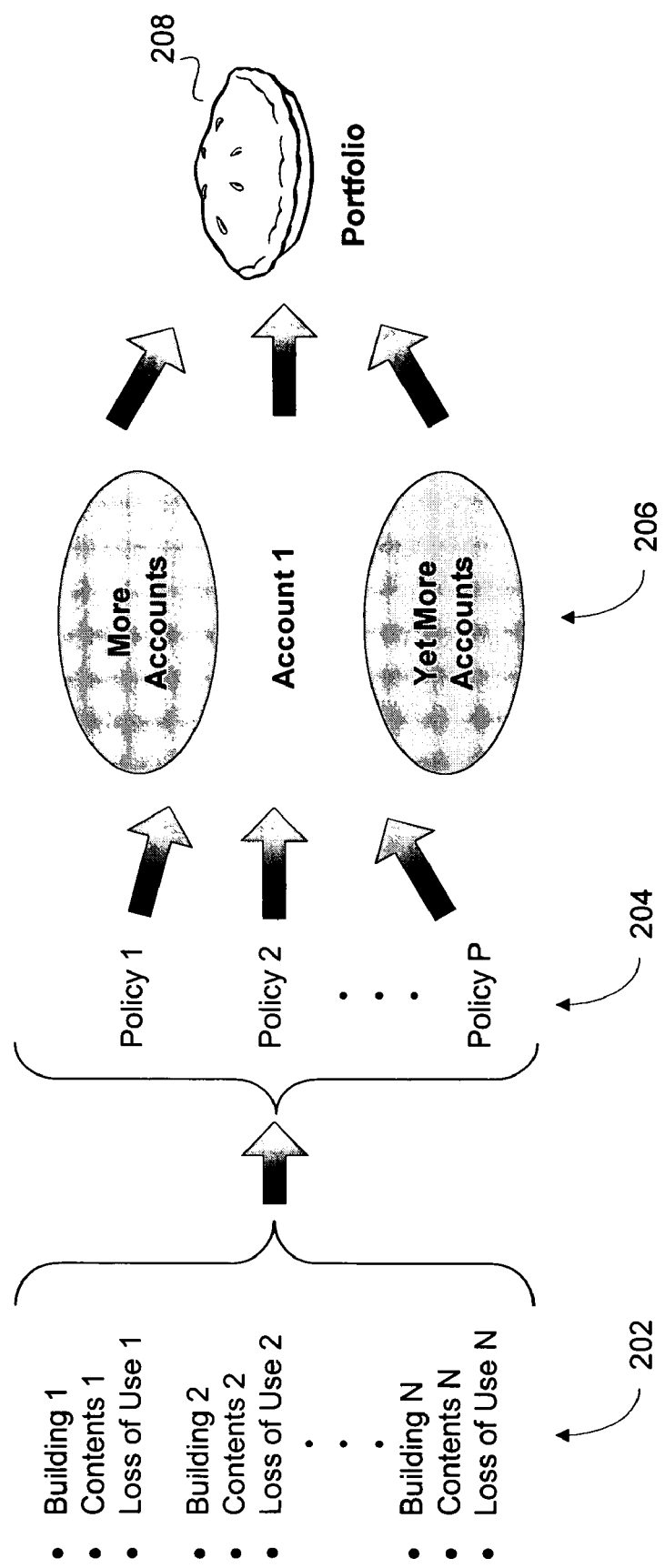
FIG. 2 is a block diagram illustrating exemplary relationships between insured properties, policies, accounts and a portfolio.

FIG. 2 is a block diagram illustrating an exemplary relationship between insured properties 202, polices 204, accounts 206 and a portfolio 208. A portfolio 208 may include one or more accounts 206. One or more of the accounts 206 may be associated with one or more clients. The accounts 206 may be associated with a portfolio 208 based on common factors such as common client (since a client may have more than one account), common location, common policy types, common peril types, and/or other commonalities. An account 206 may be associated with one or more policies 204. Each policy may be associated with one or more insured properties 202, which may include buildings, their contents and the loss of use of the building. Each of the insured properties 202 may be associated with a locational address (e.g., longitude/latitude coordinates). The policies 204 associated with an insured property 202 may typically define the liability of the property between the insured and the insurer. Treaties may further define who else (e.g., re-insurer) may be liable for the loss of the insured property. Sometimes, a building, its contents and the loss of use of the building may be covered by more than one policy.

The liability of various parties, such as the insured, the insurer, reinsurer, and other liable parties, may be defined by a financial perspective. A financial perspective may divide the liability of a total loss (of a, for example, insured property) into segments. For instance, the total loss may include a group up loss, a client loss, a gross loss, a net loss, a reinsurance net loss, and other types of loss. The ground up loss may be the total financial loss (exposure), regardless of the insurance structure, when the insured property is a total loss. The client loss may be the insured's loss below the deductible. The gross loss may be the insurer's loss after policy deductibles and other limits but before any reinsurance. The net loss may be the insurer's loss after subtracting deductibles and other limits and re-insurer's (if there are any) share is deducted. The re-insurer's net loss is the re-insurer's share of the total loss.

A financial perspective may set out the financial structure of an insured property (as it relates to either property loss and/or workmen's compensation). That is, it may specify, for example, which parties (e.g., the insured, the insurer, re-insurer, and other parties who may be liable for the loss of an insured property) are financially responsible for what portion of a loss of an insured property.

Figure 3:
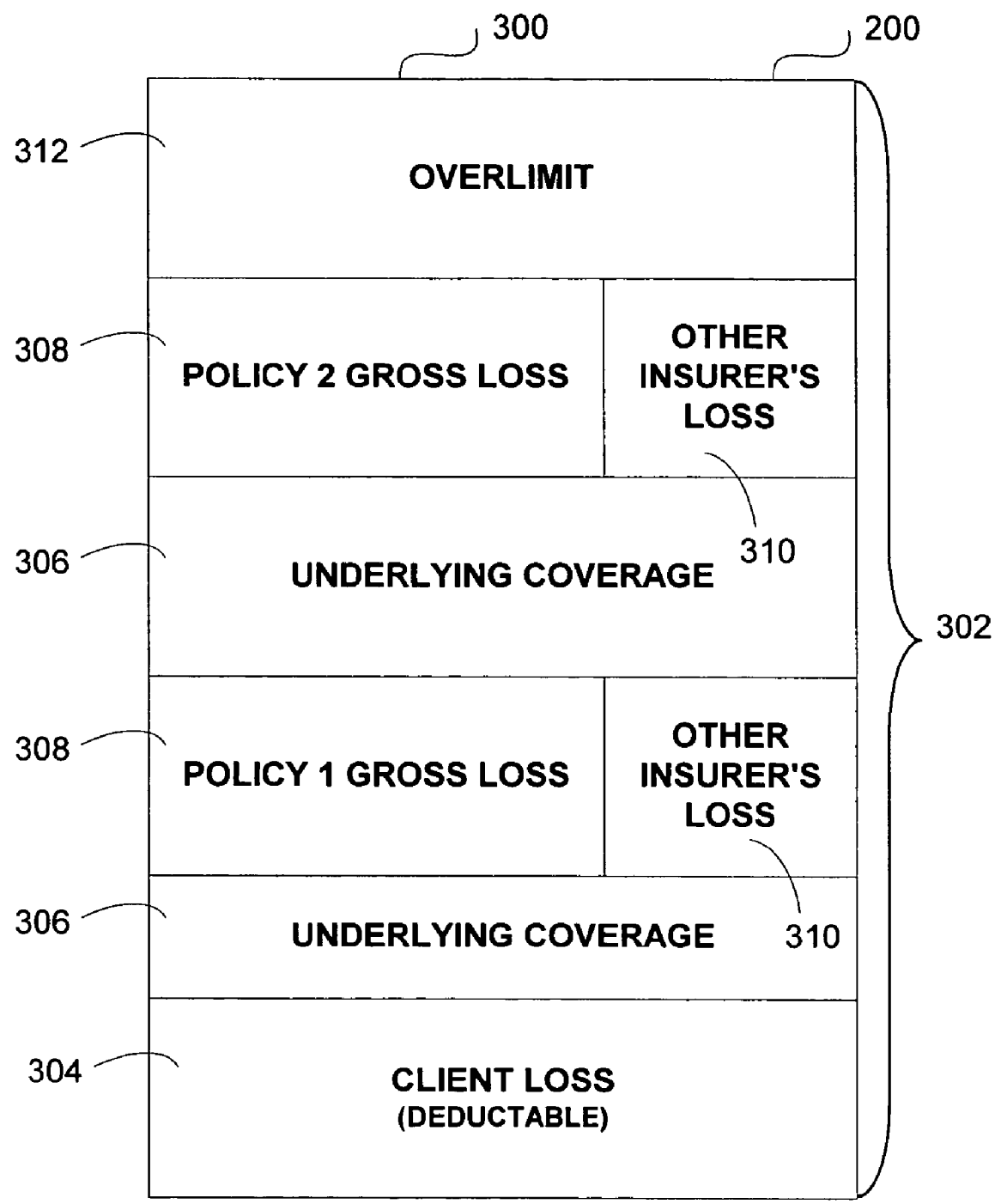
FIG. 3 is a block diagram illustrating an exemplary financial perspective.

FIG. 3 illustrates an exemplary financial perspective 300. Financial perspective 300 identifies how various parties are liable for various portions of a total liability (i.e., ground up loss) of an insured property. In this example, the entire height 302 of the financial perspective 300 represents the total liability of an insured property. The very bottom section is a client loss portion 304. This is typically incurred by an insured as a result of deductibles. The underlying coverage 306 is the loss below the insurer's attachment point. Each insured property may be covered by more than one policy. In this example, two policies, policy 1 and 2, cover the same insured property. The gross loss 308 is the insurer's loss after policy deductibles, attachment point, and limits are applied but before any reinsurance. Often an insurer will reduce risk by selling all or part of policies to other insurers. In this example, the primary insurer reduces liability for both policies by using other insurers. The other insurer's loss is the portion not included in the primary insurer's share that may be borne by other insurers. The overlimit portion 312 is the loss in excess of policy amounts. This loss is typically borne by the insured. Other parties such as reinsurers (not depicted) may also assume certain loss which may further reduce the actual liability of the primary insurer. As shown, the actual liability of a primary insurer may be substantially less than the full value of the policy or policies underwritten for a property.

FIG. 4 illustrates a process 400 for determining concentrations of exposure according to one embodiment of the invention. The process 400 may begin when exposure data or other data used to determine exposure data (e.g., policy, account, portfolio, financial perspective, treaties, and other items) is stored and organized at 402. This operation may be disregarded, particularly if, for example, the exposure data is already stored and organized. In order to find areas of high exposure concentrations, certain parameters may be provided at an operation 404. Once the parameters are established, geographical areas or locations having high concentration of exposure may be determined by implementing a concentration of exposure operation which analyzes one or more areas of analysis at an operation 406. During the implementation of the concentration of exposure operation 406, exposure data may be retrieved and/or parsed at an operation 408. Once the areas or locations of high concentration of exposure have been determined, an output may be generated at 410.

The operation for storing and organizing exposure data 402 may include an operation for linking exposure data to one or more portfolios, one or more accounts, one or more policies, and/or one or more locations. This operation 402 may further include operations for storing and linking treaties, policy information, portfolio information, account information, financial perspectives, and other information that may be used in determining exposure amounts for exposure locations.

Exposure data for each location may be for property loss or workmen's compensation or for both property loss and workmen's compensation. The operation for defining parameters 404 may include defining a region of interest, a boundary of areas of analysis, a grid size, a threshold amount, a number of areas of analysis to be indicated as being areas of high exposure concentration, and other parameters useful in determining areas of high exposure concentration. A region of interest may be the geographical area in which the process 400 determines areas of high concentration of exposure. Areas of analysis may be the geographical areas that are separately analyzed to determine each area's net exposure. The boundaries of the areas of analysis may typically be a set shape, such as a circle, square, rectangle or other shape. If the boundaries are a circle, then a radius may be provided. If the boundaries of areas include a rectangle or a square, the width and length may be provided. The threshold amount may be a result of parameter and may be set forth in an exposure threshold amount that must be exceeded in order for an area of analysis to be considered a high exposure concentration area. The number of areas of analysis to be indicted as being areas of high exposure concentration may also be another results parameter and may be used to show, for example, the "top ten" areas having the highest exposure concentrations.

According to another embodiment of the invention, the process for determining concentrations of exposure 400 may further include the operation of defining and locating exposure locations. An exposure location may be any location with a potential financial liability. The exposure locations may be identified by using precise locations of exposure via, for example, longitude/latitude coordinates, street address, building name, zip code, and other techniques for identifying locations. The exposure locations may also be assigned to location identifications.

According to another embodiment of the invention, the operation for determining concentrations of exposure 406 may use an exhaustive search approach. The exhaustive search approach determines the exposure amounts for each area (i.e., area of analysis) within the region of interest. The region of interest may be the geographical area that is of interest in determining the exposure concentrations. For example, an insurer may be interested in finding concentrations of exposures for a city. In this case, the region of interest would be the city.

Figure 5A:
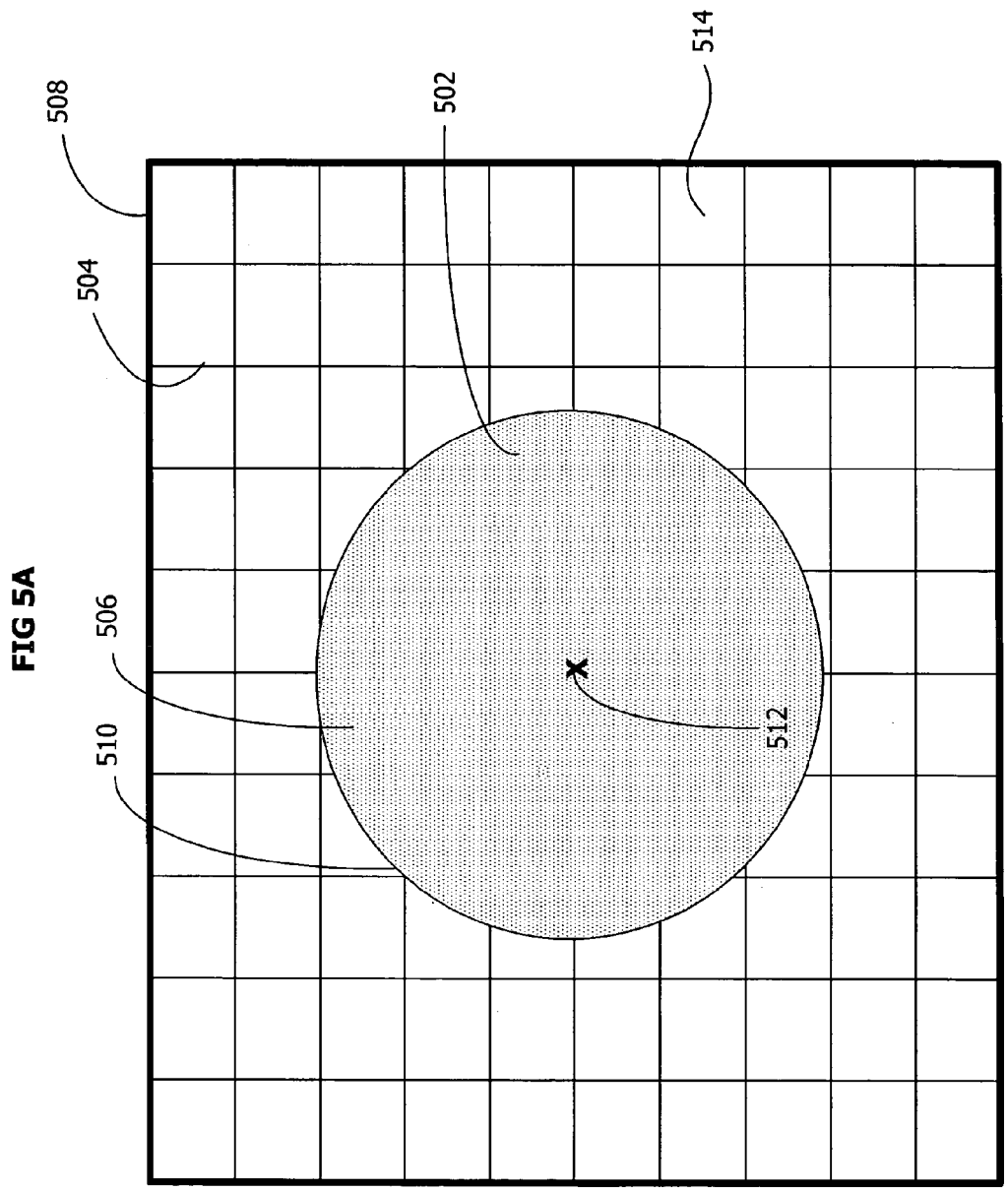
FIG. 5A illustrates an exemplary relationship between exposure location, grid, area of analysis, region of interest and area of analysis boundary.

FIG. 5A illustrates the relationship between exposure location 502, grid 504, area of analysis 506, region of interest 508 and area of analysis boundary 510 and grid cells 514. When the exhaustive search approach is implemented, the area of analysis boundary 510 (in this case, the boundary 510 is a circle that is centered at a centroid 512 as the center of one of the grid cells 514) is moved around the region of interest 508. Each time the boundary 510 moves to a new location, a new area of analysis 506 is formed. The area of analysis 506 is the area that is bounded by the boundary 510. In some embodiments, an exposure amount is determined for each area of analysis 506. Although, in this embodiment, the boundary 510 (and the resulting area of analysis 506) is a circle, the boundary 510 may be other shape types such as rectangle, oval, square, or other geometric shape.

Figure 5B:
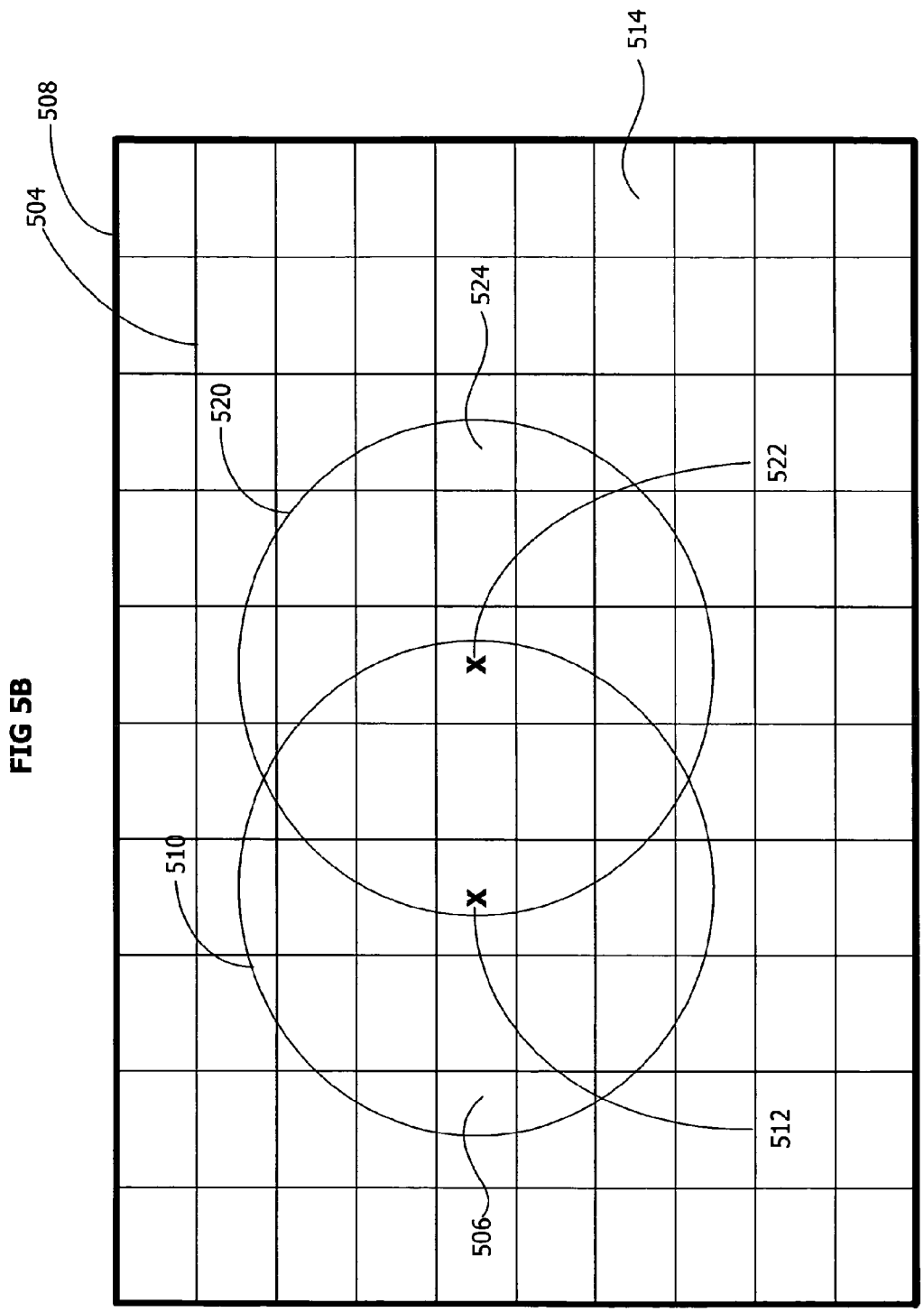
FIG. 5B illustrates an exemplary movement of an area of analysis boundary according to an embodiment of the invention.

The movement of the boundary 510 to form new areas of analysis 506 may be arbitrary or may be systematic. For example, according to one embodiment of the invention, the boundary 510 is moved by moving the centroid 512 of the circle boundary 510 from the center of one grid cell 514 to the center of the next grid cell 514 as illustrated in FIG. 5B. This results in a new area of analysis 524. In some embodiments of the invention, the new area of analysis 524 overlaps the old area of analysis 506. Once the boundary has moved to the new location, a net exposure amount for the new area of analysis 524 may be determined. According to another embodiment of the invention, the total exposure for an area of analysis 506 may be determined by totaling the net exposures for each exposure locations 502 located within the area of analysis 506.

According to an embodiment of the invention, the net exposure for each exposure location 502 may be exposures for property loss only, for workmen's compensation loss only, or for both property and workmen's compensation loss. As a result, the total exposure for an area of analysis may likewise be exposures for property loss only, for workmen's compensation loss only, or for both property and workmen's compensation loss. The property loss exposure may be associated with a specific peril such as earthquakes, tornados, terrorist attacks, windstorms, or other manmade or natural perils. Alternatively, the property loss exposure may be associated with two or more of the perils or from all perils or portions thereof.

FIG. 6 illustrates a process 600 for determining concentrations of exposure using the exhaustive search approach according to an embodiment of the invention. The process 600 may begin when the region of interest 508 is selected or otherwise provided at an operation 602. This may be accomplished, for example, by identifying the longitude/latitude coordinates (or other techniques for locating a geographical area) for the region. The boundary 510 for the area of analysis 506 may be provided at an operation 604. The boundary 510 may determine the shape of the area of analysis 506. If the boundary is a circle, as illustrated in FIGS. 5A and 5B, a radius or diameter may be provided. A grid may be created at operation 606. In order to create a grid, the dimensions of the grid cell 514 may be provided. For example, if the grid cell is a rectangle, the height and width of the grid cell may be provided.

Mapping tables may be created at an operation 608. Examples of mapping tables may include account mapping tables, policy mapping tables and location mapping tables. According to one embodiment of the invention, the process 600 uses a bottom-up rather than a top-down approach. The bottom-up approach identifies the exposure location first, then identifies the accounts associated with the location, and finally identifies the policies associated with the accounts. The tables created may facilitate the implementation of the bottom-up approach. The account mapping table may be used to find the immediate policy position for a given account. The policy mapping table may be used to find the immediate exposure location position, policy coverage file position and layer input file. The location mapping table may be used to find the account and the policy that a given exposure location belongs to, and also to find the location coverage file position and the layer input position for the given location. These tables may facilitate the determination of net exposure for an exposure location. By creating these tables, an exposure location may be linked to specific policies, accounts, portfolios, treaties and other items useful in determining a net exposure amount for the exposure location. Further, by creating these tables, the financial perspectives associated with an exposure location may be determined. Additional tables may also be created. These may include, for example, an account trigger-flag table and a location trigger-flag table. An area of analysis 506 may be selected for determining an exposure level at an operation 610. Once an area of analysis 506 is selected, the exposure for that area 506 may be determined at an operation 612. A determination may then be made as to whether there are any more areas of analysis 506 to be checked at an operation 614. If there are more to be checked, then the process 600 returns to operation 610. If not, then the exposure levels for each of the areas of analysis 506 that were determined may be analyzed and/or compared at an operation 616. For example, this may include determining whether any of the exposure concentrations exceed a threshold level or which areas of analysis 506 have the highest exposure concentrations.

Once the analysis and/or comparisons are complete, an output may be generated. The output may be in text form listing the area or areas of analysis 506 with the highest or high exposure concentrations. The output may also be in a graphical form such as charts or may be displayed on a map showing the location or locations having the highest or high exposure concentration. If the output is a map, then areas of high exposure concentration may be indicated by highlighting the areas using different colors or other mapping techniques for indicating or highlighting a location. The specific colors used in output map may have specific meaning such as using red for the highest concentration areas.

Grid 504 may be used to determine which exposure locations are to be included when determining the exposures for areas of analysis 506. Each grid cell 514 may contain zero, one or more exposure locations 502. Each grid cell 514 may be associated with a list of exposure locations 502 that are inside the grid cell 514. According to one embodiment of the invention, only those exposure locations 502 that are within the area of analysis 506 are considered when determining exposure level for that area of analysis 506. In order to speed up the process for determining which exposure locations 502 are within an area of analysis 506, each exposure location 502 that belongs to a grid cell 514 that is completely within the area of analysis 506 are automatically assumed to be in the area of analysis 506. If an exposure location 502 is located in a grid cell 514 that is completely outside the area of analysis 506 then that exposure location 502 is disregarded during the process for determining the total exposure for the area of analysis 506. Only those exposure locations 502 that are partially in grid cells 514 are individually checked to determine whether they are in the area of analysis 506. These steps may reduce the processing time to determine which exposure locations 502 are within an area of analysis 506. According to another embodiment of the invention, if the area of analysis 506 is a circle, as illustrated in FIGS. 5A and 5B, then a table with the size of (Radius/GridWidth+1)**2, which is the maximum number of grid cell 514 within a circle, may be crated. Any grid cell 514 which is completely in the circle may be saved starting from bottom up, and any grid cell 514, which will only be partially in the circle, may be saved from the top-to-bottom. This table may provide a clear picture of which grid cells 514 are in the circle and which grid cells 514 are not.

According to another embodiment of the invention, if the areas of analysis 506 are circles then the size of a grid cell 514 may be determined per analysis and may depend on the radius of the circles. Generally, the ratio of grid width to radius (radius of the circular area of analysis 506) may have an impact on the accuracy and performance of the analysis. The grid width ratio (grid width/radius) may be pre-set or may be defined for each analysis performed. To determine the accuracy of the analysis using different grid width ratios, two elements may be measured: the positional accuracy of the areas that are identified by the analysis, and the resulting affect on the amount of exposure accumulation in each area. As to the first element, the first element refers to the ability to determine the actual area of high exposure concentration. Referring again to FIG. 5B illustrating two areas of analysis 506 and 524, if the area of analysis boundary 510 is being moved in a systematic manner to define areas of analysis 506, positional inaccuracy may occur. For example, suppose the movement of the boundary 510 is dictated by moving the centroid of the boundary 510 from the center of one grid cell 514 to the center of the next grid cell 514 as illustrated in FIG. 5B. An error may occur because the actual area having the highest or high exposure concentrations may be a circle between the two circles 510 and 520. That is, the area of highest or high exposure concentration may be an area defined by a circle with a centroid between the two other centroids 512 and 522. This would result in a positional inaccuracy.

Although positional accuracy may be important, another consideration may be the amount of exposure accumulation within the circle and the potential error introduced because the area may not be centered accurately. There appears to be some trade-off between improving positional accuracy as opposed to improving the accuracy of exposure accumulation. The grid width ratio may be selected to fully maximize performance. In one embodiment, a default grid width ratio may be set at 0.25. In tests conducted using different radii, a grid width ratio of 0.25 resulted in the potential error in positional accuracy of approximately ±9% for a given circle. The tests also revealed that the amount of exposure accumulation was generally within ±3% for all radii, and typically an exact match for small radius (500 meter) tests. However, the analysis run time typically increased as the grid width ratio becomes smaller.

In order to minimize the magnitude of error in positional accuracy, in one embodiment of the invention, a maximum grid size of 1000 meters (for square grid cells) may be set as the default grid size. The maximum grid width may then be triggered at a radius greater than 4,000 meters. For radii less than 4,000 meters, the amount or potential inaccuracy may be dependant on the grid width ratio. For radii greater than 4,000 meters, the potential inaccuracy was found to be capped at approximately 700 meters. Generally, performance was found to degrade as the radius is increased relative to running the analysis without a maximum in place.

FIG. 7 illustrates a process 700 for determining the net exposure amount for an area of analysis 506 according to an embodiment of the invention. An operation 702 determines which grid cells 514 are in the area of analysis 506, which grid cells 514 are out of the area of analysis 506, and which grid cells 514 are partly in the area of analysis 506. Next, a determination may be made as to which exposure locations 502 are in the area of analysis at an operation 704. As described above, only those exposure locations 502 that are located in grid cells 514 that are completely in the area of analysis 506 are automatically determined to be in the area of analysis 506. After determining which exposure locations 502 are in the area of analysis 506, the net exposure for each of the exposure locations 502 located within the area of analysis 506 is determined in an operation 706. This may be accomplished, for example, by using mapping tables as described earlier. Once the net exposure amounts for each exposure location 502 is determined, the net exposures may then be added together to produce the total exposure amount for the area of analysis 506 at an operation 708.

According to another embodiment of the invention, the loss structure for an area of analysis 506 may be a specific area model or damage footprint model. Using a specific area model, all of the locations located within the area of analysis 506 may experience a complete (i.e., 100 percent) loss. Within a damage footprint, different sections of the area of analysis 506 may experience different levels of loss. Therefore, in order to determine the exposure amount for each of the exposure locations 502 that fall into the area of analysis 506, a determination is made as to which levels of loss (e.g., percent loss) is to be attached to each of the exposure locations 502. Once the level of loss for an exposure location 502 has been determined (along with the mapping tables), the net exposure amount for the exposure location may be determined.

According to another aspect of the invention, the operation for determining concentrations of exposure 406 may utilize an analytical approach. The analytical approach may use density functions in order to locate peaks which may indicate locations of high exposure concentrations.

According to an embodiment of the invention, the analytical approach is implemented by using a square (or rectangle) to approximate an area of analysis that is a circle. For example, suppose we know the distribution of our interested values which is defined as f(x,y). Then for a given area, we want to maximize the following equations:

$$\max(\int f(x,y)dxdy)$$

Suppose the area is rectangle, the area being defined as Dx,Dy. Suppose further that the centroid location is X0,Y0, then:

$$G(X0,Y0) = \max(\int_{X0-Dx}^{X0+Dx} dx \int_{Y0-Dy}^{Y0+Dy} f(x,y)dy)$$

For any peak or valley for the above equation, $$\frac{\partial G(X0,Y0)}{\partial X0} = 0 \quad\quad 1.1$$

$$\frac{\partial G(X0,Y0)}{\partial Y0} = 0 \quad\quad 1.2$$

Based on 1.1, $$\int_{Y0-Dy}^{Y0+Dy} [f(X0+Dx,y) - f(X0-Dx)]dy = 0 \quad\quad 2.1$$

And from 1.2, $$\int_{X0-Dx}^{X0+Dx} [f(x,Y0+Dy) - f(x,Y0-Dy)]dx = 0 \quad\quad 2.2$$

From equations 2.1 and 2.2, the following equations will follow:

$$(Fy(X0+Dx, Y0+Dy) - Fy(X0+Dx, Y0-Dy)) - (Fy(X0-Dx, Y0+Dy) - Fy(X0-Dx, Y0-Dy)) = 0$$

$$(Fx(X0+Dx, Y0+Dy) - Fx(X0-Dx, Y0+Dy))(Fx(X0+Dx, Y0-Dy) - Fx(X0-Dx, Y0-Dy)) = 0$$

Suppose further that the region is divided into grids. The above two equations must be true for any given grid (i,j) which contains a peak.

If we assume that the value we are interested in at grid (i,j) is Value(Xi,Yj), then we have the following recursive equations for Fx(Xi,Yj), Fy(Xi,Yj):

$$Fy(Xi,Yj) = Fy(Xi,Yj-1) + \text{Value}(Xi,Yj) - \text{Value}(Xi,Yj-1-Dy)$$

$$Fx(Xi,Yj) = Fx(Xi-1,Yj) + \text{Value}(Xi,Yj) - \text{Value}(Xi-1-Dx,Yj)$$

So for any peaks in (Xi,Yj):

$$(Fy(Xi+Dx, Yj+Dy) - Fy(Xi+Dx, Yj-Dy)) - (Fy(Xi-Dx, Yj+Dy) - Fy(Xi-Dx, Yj-Dy)) = 0$$

$$(Fx(Xi+Dx, Yj+Dy) - Fx(Xi-Dx, Yj+Dy)) - (Fx(Xi+Dx, Yj-Dy) - Fx(Xi-Dx, Yj-Dy)) = 0$$

For the density function f(x,y), assume that the whole region is divided into Nx*Ny grids, and the value at grid (i,j) is Value(Xi,Yj), then $$f(Xi,Yj) = \text{Value}(Xi,Yj)/\text{Sum}(\text{Value}(Xi,Yj)).$$

In this approach, rectangles are used to approximate circles and to find all of the peaks existing in the region and localize the circle peak values. The advantages of this approach is that it will likely find the real peaks. However, the goal is not necessary to find peaks. That is, some concentration of exposures may not actually be peaks. Thus, this approach may not be robust. This recursion property may only apply to exposure/ground up loss (e.g., assuming 100% total loss). Thus, when a financial structure needs to be applied, this approach may not be the optimal solution.

According to another embodiment of the invention, the process for determining concentrations of exposure 400 may further comprise an operation for performing a specific area analysis, a damaged footprint analysis and/or a building level analysis. The specific area analysis determines the exposure amount for a specified area or an area surrounding a specified target. According to one embodiment, the area is a circle with the centroid located at the target location if there is one. The analysis assumes complete (i.e., 100 percent) ground up property loss and a user specified casualty distribution to all locations within the circle. In the damaged footprint analysis, an area of interest (such as a circle) is defined. Rather than specifying the radius of the circle, a method of attack may be selected. The method of attack determines the levels of loss within the circle. That is, instead of assuming a uniform loss within the circle, such as specific area analysis, the method of attack plots several concentric rings within the circle (like a bull's eye), each ring represents a different ground up loss percentage and casualty distribution. The building level analysis may be used to monitor a specific building or multiple buildings. This analysis returns the exposure accumulations by building, either for all buildings in a portfolio or for specific buildings.

In order to perform these analyses, profiles for each of these analyses may be created. An analysis profile may include information, such as parameters, used in performing the analysis. Certain generic operations may be performed in order to create a profile for the analysis. FIG. 8 illustrates a process 800 for generic operations that may be performed in order to create an analysis profile according to an embodiment of the invention. Process 800 includes an operation 802 for selecting a coverage to accumulate such as property coverages and/or workmen's compensation. If workmen's compensation is selected, different levels of losses may be defined. These levels may include, for example, minor injuries, serious injuries, permanent disabilities, and fatalities. Each of these levels may represent different percentage losses. For instance, fatalities would be a 100 percent, while minor injuries may be, for example, 5 percent. An operation 804 identifies one or more financial perspectives that set forth the structure of the coverage (e.g., who is responsible for what amount of injured loss) and may be used in order to determine net loss or exposure. An operation 806 for defining output preferences may also be performed. Output preferences determine the type and format of the output. For example, it may be desirable to see the distance between exposure locations and the centroid of the area being evaluated. If the analysis includes workmen's compensation exposure, the output may include a loss for each type of injury per area, per location. These operations may be independent from each other and may be performed in any order as would be apparent.

In addition to the generic operations listed above, other operations may be performed for creating each of the analysis' profiles. For instance, for the specific area analysis profile, an operation for identifying the area of analysis may be performed. Such an operation may include defining the centroid location of the area being analyzed by latitude/longitude coordinate, radius, and units (feet or meters). Alternatively, a stored centroid may be used and only the radius has to be identified. In yet another alternative, a stored area may be used. Note that in each of the analysis described here, multiple areas may be analyzed (i.e., accumulated) at the same time. For each area to be analyzed, the above operations for identifying the location of the area may be performed.

For the damage footprint profile, the method of attack may provide the radii to be used. Thus, only the target location (e.g., centroid) may need to be provided or otherwise identified. In an alternative embodiment, however, both the target location and the radii (if the area being analyzed is a circle) may be provided or otherwise identified. An operation may be performed for the damage footprint profile to determine the damage footprint. That is, an operation to determine the levels of loss for each, for example, concentric circle. Alternatively, predetermined levels of loss may be used instead.

For the building level profile, an operation may be performed that determines whether to analyze every building in a portfolio, an account or selecting specific buildings for analysis.

Additional features and advantages of the invention are set forth in the description that follows, and in part are apparent from the description, or may be learned by practice of the invention. The objectives and other advantages of the invention are realized and gained by the structure particularly pointed out in the written description and claims thereof as well as the appended drawings.

Although particular embodiments of the present invention have been shown and described, it will be understood that it is not intended to limit the invention to the embodiments described above and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims.

What is claimed is:

1. An exposure analyzing system, comprising:
one or more processors; and
a memory operatively coupled to the one or more processors, the memory for storing instructions which, when executed by the one or more processors, causes the one or more processors to define a first set of a plurality of parameters, wherein the first set of the plurality of parameters define a region of interest, divide the region of interest into a grid having a plurality of grid cells, wherein at least one of the plurality of grid cells includes at least one exposure location, define a second set of a plurality of parameters, wherein the second set of the plurality of parameters define an area of analysis, iteratively position the area of analysis throughout the region of interest, wherein each iterative position of the area of analysis in the region of interest includes a respective plurality of grid cells, determine a concentration of financial exposure for each iterative position of the area of analysis, and use a financial analysis associated with each exposure location to determine the concentration of financial exposure, wherein the financial analysis includes one or more of a total exposure of an area assuming 100 percent loss for the entire area, total loss of an area with different levels of loss for different sections of the area, or exposure for one or more buildings.

2. The system of claim 1, further comprising a database.

3. The system of claim 2, wherein the database comprises a mapping table.

4. The system of claim 3, wherein the mapping table is at least one of a location mapping table, a policy mapping table and an account mapping table.

5. The system of claim 2, wherein the database includes financial perspective data.

6. The system of claim 1, wherein the system further comprises at least one of a specific area analyzer module, a damage footprint analyzer module, and a building level analyzer.

7. The system of claim 1, further comprising an input/output device for generating output in a map format.

8. The system of claim 1, wherein the memory for storing instructions which, when executed by the one or more processors, causes the one or more processors to link the financial exposure to at least one of one or more portfolios, one or more accounts, one or more policies or one or more locations.

9. The system of claim 1, wherein the memory for storing instructions which, when executed by the one or more processors, causes the one or more processors to determine which of the iterative positions of the area of analysis exceed a threshold level of financial exposure.

10. The system of claim 1, wherein the memory for storing instructions which, when executed by the one or more processors, causes the one or more or more processors to define a boundary of the area of analysis.

11. The system of claim 10, wherein the boundary of the area of analysis is one of a circle, a square, or a rectangle.

12. The system of claim 1, wherein the at least one exposure location includes potential levels of liability.

13. The system of claim 1, wherein the memory for storing instructions which, when executed by the one or more processors, causes the one or more processors to define a default grid size.

14. The system of claim 9, further comprising an output device configured to output only the areas of analysis that exceed the threshold level of financial exposure.

15. The system of claim 10, wherein the boundary of the area of analysis is a circle and wherein the ratio of grid width to circle radius maximizes positional and exposure accuracy.

16. A non-transitory computer storage medium encoding computer executable instructions that when executed by a processor perform a method for determining financial exposure of a geographic region of interest, the method comprising:
defining a first set of a plurality of parameters, wherein the first set of the plurality of parameters define a region of interest;
dividing the region of interest into a grid having a plurality of grid cells, wherein at least one of the plurality of grid cells includes at least one exposure location;
defining a second set of a plurality of parameters, wherein the second set of the plurality of parameters define an area of analysis;
iteratively positioning the area of analysis throughout the region of interest, wherein each iterative position of the area of analysis in the region of interest includes a respective plurality of grid cells;
determining a concentration of financial exposure for each iterative position of the area of analysis; and
using a financial analysis associated with each exposure location for determining the concentration of financial exposure;
wherein the financial analysis includes one or more of a total exposure of an area assuming 100 percent loss for the entire area, total loss of an area with different levels of loss for different sections of the analyzed area, or exposure for one or more buildings.

17. The method of claim 16, further comprising linking the financial exposure to at least one of one or more portfolios, one or more accounts, one or more policies or one or more locations.

18. The method of claim 16, further comprising storing the concentration of financial exposure for each iterative position of the area of analysis in a database.

19. The method of claim 16, further comprising determining which of the iterative positions of the area of analysis exceed a threshold level of financial exposure.

20. The method of claim 16, further comprising defining a boundary of the area of analysis.

21. The method of claim 20, wherein the boundary of the area of analysis is one of a circle, a square, or a rectangle.

22. The method of claim 16, further comprising determining which of the iterative positions of the area of analysis have a highest concentration of financial exposure.

23. The method of claim 16, further comprising defining a default grid size.

24. The method of claim 19, further comprising only outputting the areas of analysis that exceed the threshold level of financial exposure.

25. The method of claim 20, wherein the boundary of the area of analysis is a circle and wherein the ratio of grid width to circle radius maximizes positional and exposure accuracy.

* * * * *

UNITED STATES PATENT AND TRADEMARK OFFICE
CERTIFICATE OF CORRECTION

| | | |
|---|---|---|
| PATENT NO. | : 8,380,545 B2 | Page 1 of 1 |
| APPLICATION NO. | : 12/764045 | |
| DATED | : February 19, 2013 | |
| INVENTOR(S) | : Han Chen et al. | |

It is certified that error appears in the above-identified patent and that said Letters Patent is hereby corrected as shown below:

In the Specification

Column 2, line 1, replace "is, may" with --is, it may--
Column 6, line 23, replace "block diagram" with --diagram--
Column 6, line 40, replace "amount of an" with --amount for an--
Column 7, line 3, replace "specific geographical location" with --specific geographical locations--
Column 7, line 34, replace "80 may" with --80, may--
Column 7, line 39, replace "represents exposure" with --represents the exposure--
Column 7, line 61, replace "Internet, the" with --Internet, an--
Column 8, line 40, replace "block diagram" with --diagram--
Column 8, line 41, replace "polices" with --policies--
Column 8, line 65, replace "group" with --ground--
Column 9, line 7, replace "and re-insurer's" with --and the re-insurer's--
Column 9, line 26, replace "policy 1 and 2" with --policy 1 and policy 2--
Column 9, line 32, replace "insurer's loss is" with --insurer's loss 310 is--
Column 10, line 17, replace "result of" with --result--
Column 10, line 21, replace "indicted" with --indicated--
Column 10, line 58, replace "such as rectangle" with --such as a rectangle--
Column 12, line 9, after "may be generated" insert --at an operation 618--
Column 12, line 44, replace "(Radius/GridWidth+1)**2" with --(Radius/GridWidth+1)*2--
Column 12, line 46, replace "crated" with --created--
Column 12, line 63, replace "affect on" with --effect on--
Column 13, line 28, replace "becomes smaller" with --became smaller--
Column 14, line 35, replace "f(X0-Dx)" with --f(X0-Dx, y)--
Column 15, line 54, replace "injured" with --insured--

Signed and Sealed this
Third Day of December, 2013

Margaret A. Focarino
*Commissioner for Patents of the United States Patent and Trademark Office*